(12) United States Patent
Olson et al.

(10) Patent No.: US 10,888,703 B2
(45) Date of Patent: *Jan. 12, 2021

(54) FAR FIELD TELEMETRY OPERATIONS BETWEEN AN EXTERNAL DEVICE AND AN IMPLANTABLE MEDICAL DEVICE DURING RECHARGE OF THE IMPLANTABLE MEDICAL DEVICE VIA A PROXIMITY COUPLING

(71) Applicant: MEDTRONIC, INC., Minneapolis, MN (US)

(72) Inventors: David P. Olson, Minnestrista, MN (US); William C. Phillips, Brooklyn Park, MN (US); Garrett R. Sipple, Circle Pines, MN (US); Yu Wang, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/215,918

(22) Filed: Dec. 11, 2018

(65) Prior Publication Data
US 2019/0115793 A1    Apr. 18, 2019

Related U.S. Application Data

(63) Continuation of application No. 15/650,598, filed on Jul. 14, 2017, now Pat. No. 10,177,609, which is a (Continued)

(51) Int. Cl.
*A61N 1/37* (2006.01)
*A61N 1/372* (2006.01)
(Continued)

(52) U.S. Cl.
CPC .......... *A61N 1/37252* (2013.01); *A61B 5/686* (2013.01); *A61M 5/172* (2013.01);
(Continued)

(58) Field of Classification Search
USPC ................................................ 607/32–33, 61
See application file for complete search history.

(56) References Cited

U.S. PATENT DOCUMENTS

2003/0114898 A1* 6/2003 Von Arx .................. A61N 1/08
607/60

* cited by examiner

*Primary Examiner* — Nicole F Lavert
(74) *Attorney, Agent, or Firm* — Withers & Keys, LLC

(57) ABSTRACT

Far field telemetry operations are conducted between an external device and an implantable medical device while power is being transferred to the implantable medical device for purposes of recharging a battery of the implantable medical device. The far field operations may include exchanging recharge information that has been collected by the implantable medical device which allows the external device to exercise control over the recharge process. The far field operations may include suspending far field telemetry communications for periods of time while power continues to be transferred where suspending far field telemetry communications may include powering down far field telemetry communication circuits of the implantable medical device for periods of time which may conserve energy. The far field operations may further include transferring programming instructions to the implantable medical device.

20 Claims, 10 Drawing Sheets

Related U.S. Application Data continuation of application No. 15/042,073, filed on Feb. 11, 2016, now Pat. No. 9,729,001, which is a continuation of application No. 14/246,071, filed on Apr. 5, 2014, now Pat. No. 9,318,916, which is a continuation of application No. 13/016,763, filed on Jan. 28, 2011, now Pat. No. 8,712,541.

(51) Int. Cl.
| | |
|---|---|
| *H02J 50/10* | (2016.01) |
| *H02J 50/80* | (2016.01) |
| *H02J 50/90* | (2016.01) |
| *A61N 1/378* | (2006.01) |
| *G16H 40/67* | (2018.01) |
| *A61B 5/00* | (2006.01) |
| *A61M 5/172* | (2006.01) |
| *H02J 7/02* | (2016.01) |
| *H02J 7/00* | (2006.01) |

(52) U.S. Cl.
CPC ....... *A61N 1/3787* (2013.01); *A61N 1/37217* (2013.01); *G16H 40/67* (2018.01); *H02J 7/025* (2013.01); *H02J 50/10* (2016.02); *H02J 50/80* (2016.02); *H02J 50/90* (2016.02); *A61N 1/37* (2013.01); *A61N 1/37276* (2013.01); *H02J 7/00034* (2020.01)

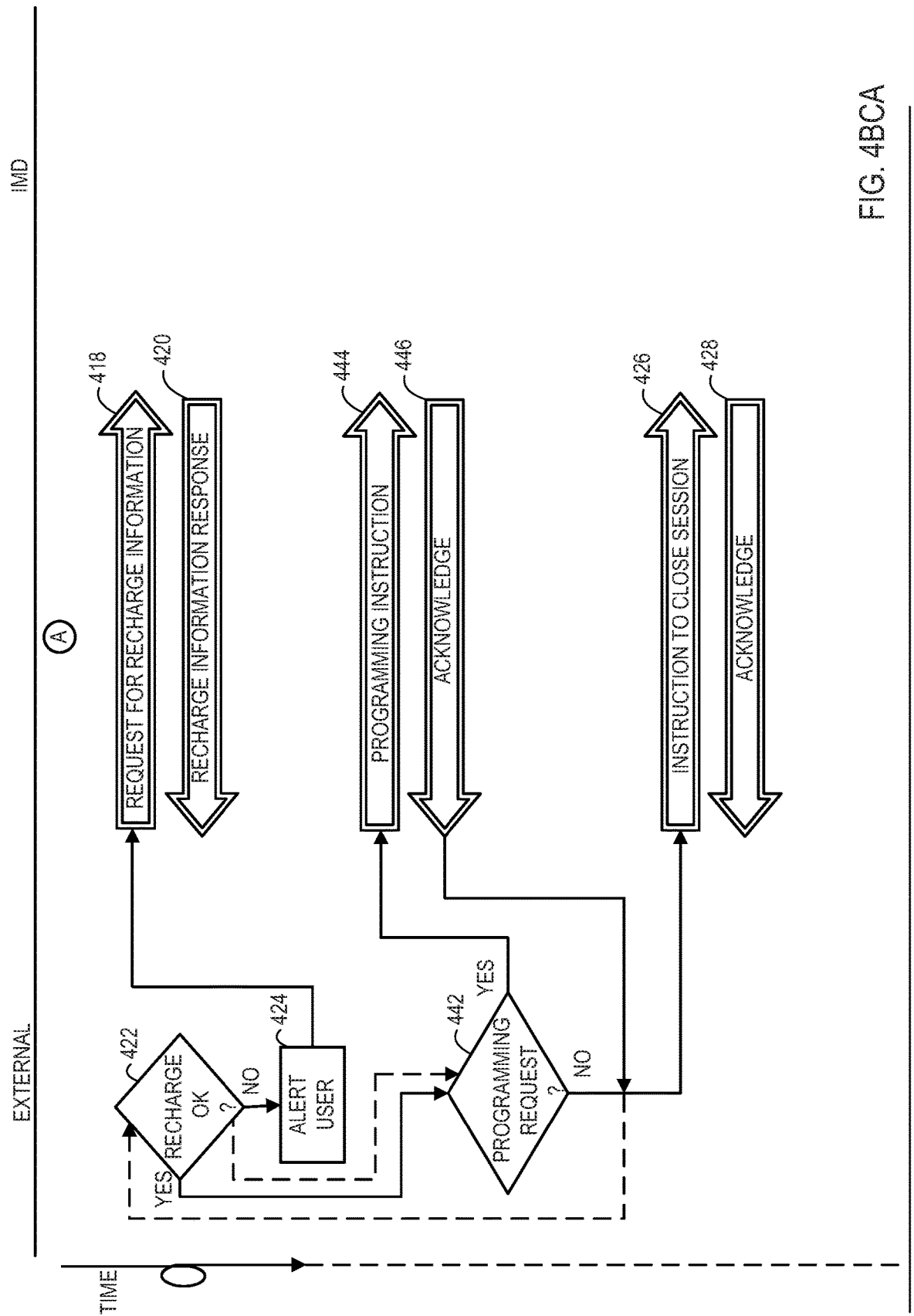
FIG. 4BCA

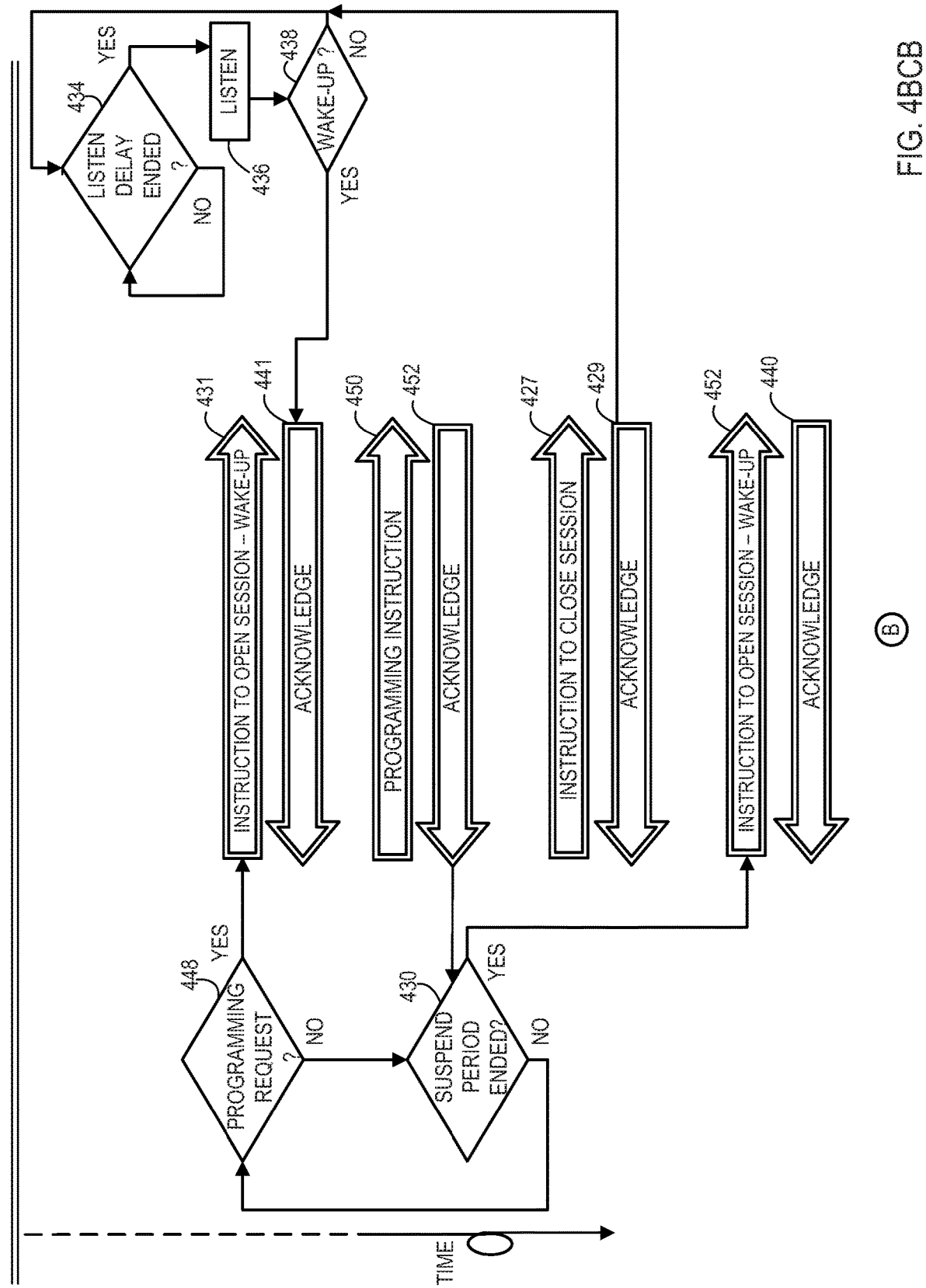
FIG. 4BCB

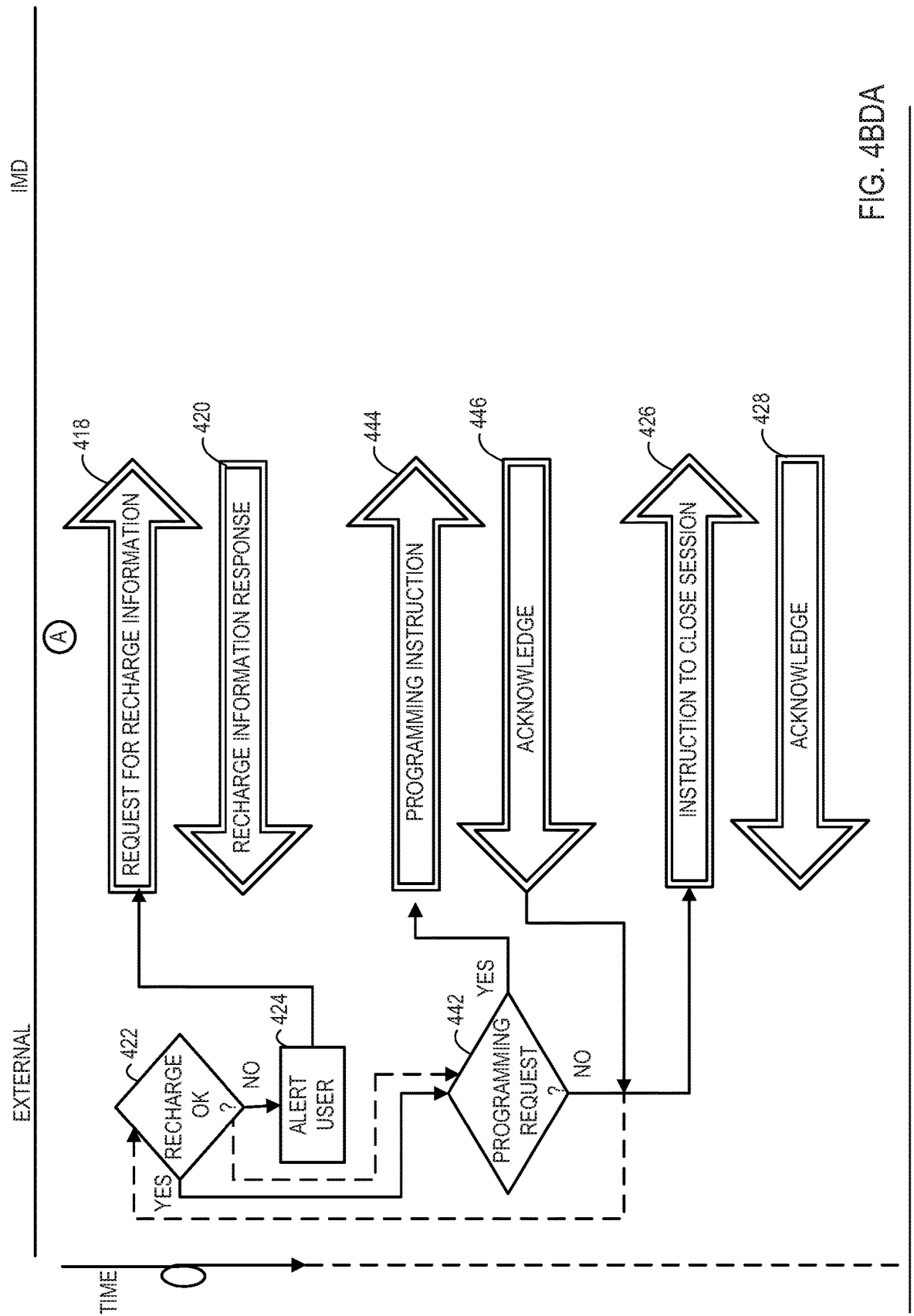
FIG. 4BDA

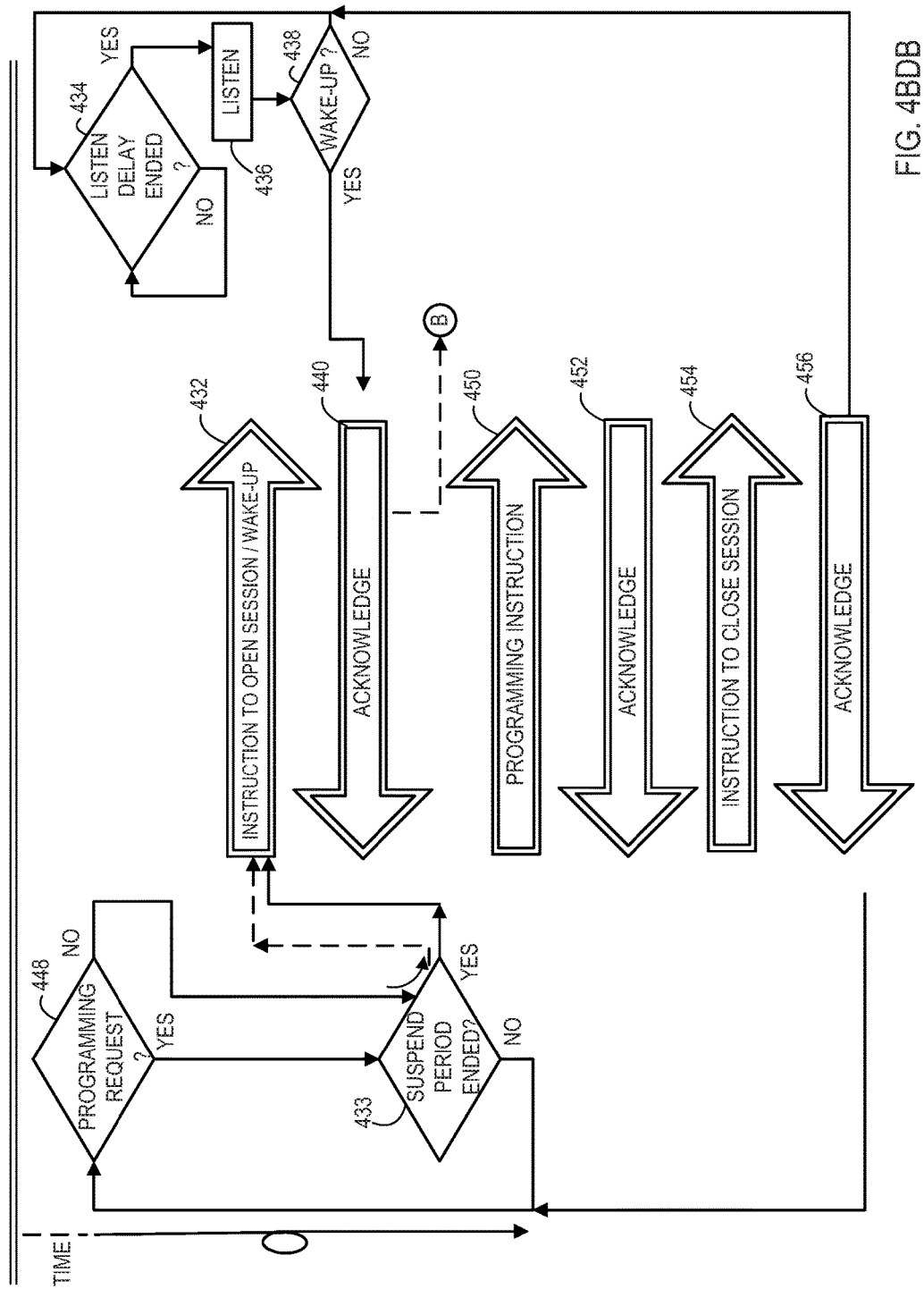

FAR FIELD TELEMETRY OPERATIONS BETWEEN AN EXTERNAL DEVICE AND AN IMPLANTABLE MEDICAL DEVICE DURING RECHARGE OF THE IMPLANTABLE MEDICAL DEVICE VIA A PROXIMITY COUPLING

RELATED APPLICATIONS

The present application is a continuation application of U.S. Pat. No. 10,177,609, filed on Jul. 14, 2017, which is a continuation of U.S. Pat. No. 9,729,001, filed on Aug. 8, 2017, which is a continuation of U.S. Pat. No. 9,318,916, filed on Apr. 19, 2016, which is a continuation of U.S. Pat. No. 8,712,541, filed on Apr. 29, 2014.

TECHNICAL FIELD

Embodiments relate to recharge sessions between an implantable medical device to be recharged and an external device in control of the recharge energy. More particularly, embodiments relate to conducting far field telemetry operations between the implantable medical device and the external device while recharge energy is being transferred.

BACKGROUND

Implantable medical devices including those that are positioned on the exterior of a body of a patient as well as those that are positioned subcutaneously or deeper typically utilize an on-board battery that allows the patient to be untethered to a power source. The patient maintains mobility while the implantable medical device performs a particular medical task by operating on power from the battery. For instance, the implantable medical device may provide stimulation therapy for neurological or cardiac conditions, may provide drug delivery for various conditions such as pain management, and/or may provide physiological monitoring.

While the on-board battery may power the medical device for a relatively long period of time, the on-board battery will eventually be depleted. Prior to rechargeable medical systems, the implantable medical device would be replaced once the battery became depleted. With rechargeable medical systems, an external device provides recharge energy over a proximity coupling, which is typically inductive, to the implantable medical device. This recharge energy restores the on-board battery to a satisfactory level for continued operation of the medical device.

During a recharge session, the external device in control of the recharge energy and the implantable medical device to be recharged exchange telemetry communications related to the recharge process. Recharge information such as battery status, coupling efficiency and the like may be transferred in this manner so that the external device can properly control delivery of the recharge energy as well as instruct a user. Conventionally, the two devices exchange telemetry communications over a proximity coupling. However, this proximity coupling is also being used to transfer the recharge energy, and in some cases recharging may stop while the telemetry communications are conducted over the proximity coupling. This increases the amount of time needed to complete the recharge session.

SUMMARY

Embodiments address issues such as these and others by providing far field telemetry operations between the external device and the implantable medical device while power continues to be transferred to the implantable medical device to recharge the battery. The far field telemetry operations include exchanging by far field telemetry communications recharge information collected by the implantable medical device that is used by the external device. The far field telemetry operations may include suspending far field telemetry communications for periods during the recharge session to reduce the amount of energy being expended by the implantable medical device during the recharge session. The far field telemetry operations may include sending programming instructions to the implantable medical device such as where the external device receives a programming request from a user during the recharge session.

Embodiments provide a method of recharging an implantable medical device. The method involves establishing a far field telemetry communication session with the implantable medical device and transferring power over a proximity coupling to the implantable medical device during the far field telemetry communication session. The method further involves receiving recharge information from the implantable medical device via the far field telemetry communication session while transferring power to the implantable medical device, and after receiving the recharge information, suspending the far field telemetry communication session for a period of time while transferring power to the implantable medical device.

Embodiments provide a medical system that includes an external device having a far field telemetry communication circuit and a recharge circuit. The external device transfers power through a recharge head of the recharge circuit while receiving recharge information through a far field telemetry communication session via the far field telemetry communication circuit. The external device suspends the far field telemetry communication session for a first period of time after receiving the recharge information by sending an instruction to close the far field telemetry communication session to the implantable medical device while continuing to transfer power. The medical system also includes an implantable medical device having a far field telemetry communication circuit and a recharge circuit. The implantable medical device receives transferred power via a proximity coupling of the recharge circuit to the recharge head of the external device while sending recharge information through the far field telemetry communication session via the far field telemetry communication circuit. The implantable medical device closes the far field telemetry communication session upon receiving the instruction and listens for an instruction to open the far field telemetry communication session after each occurrence of a second period that is no greater than the first period while continuing to receive transferred power.

Embodiments provide an implantable medical device that includes a medical circuit that performs a medical task, a battery that provides power to the medical circuit, a recharge circuit that provides power to the battery, a far field telemetry communication circuit, and a processor. The processor controls the recharge circuit and the far field telemetry communication circuit, where the processor directs the recharge circuit to receive transferred power from a proximity coupling to a recharge head of an external device. The processor directs the far field telemetry communication circuit to send recharge information via a far field telemetry communication session with the external device while the recharge circuit receives transferred power. The processor further directs the far field telemetry communication circuit to power down in response to receiving a command to close the communication session with the external device while the recharge circuit receives transferred power. The processor periodically directs the far field telemetry communication circuit to power up and listen for a command to open the communication session while the recharge circuit receives transferred power.

Embodiments provide a method of recharging an implantable medical device. The method involves establishing a far field telemetry communication session with the implantable medical device and transferring power over a proximity coupling to the implantable medical device during the far field telemetry communication session. The method further involves receiving recharge information from the implantable medical device via the far field telemetry communication session while transferring power to the implantable medical device, and while transferring power, sending programming instructions to the implantable medical device via the far field telemetry communication session.

DETAILED DESCRIPTION

Embodiments provide for far field telemetry operations during recharge sessions between an external device and an implantable medical device while the power used for recharge is being transferred to the implantable medical device over a proximity coupling. Embodiments provide for the far field telemetry operations to be suspended for periods of time while the power continues to be transferred. Embodiments further provide for the far field telemetry operations to provide programming instructions to the implantable medical device while the power continues to be transferred.

Figure 1:
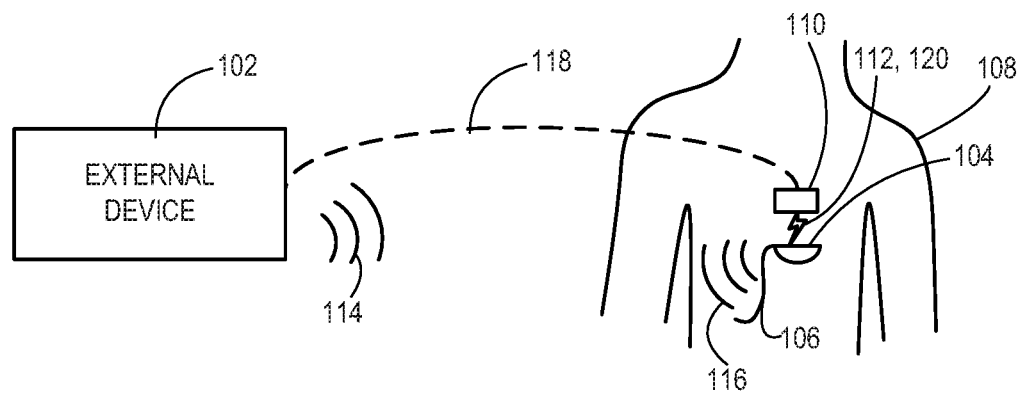
FIG. 1 shows an example of a medical system according to various embodiments.

FIG. 1 shows an environment that includes an external device 102, such as a clinician programmer-recharger or a patient programmer-recharger that is nearby a patient 108 who has an IMD 104. The IMD 104 may be implanted within or mounted externally to the body 108 and may perform one or more medical tasks such as cardiac or neurological stimulation, physiological sensing, drug infusion, and the like. The IMD 104 may include components 106 such as stimulation or sensing leads or drug delivery catheters that extend from the IMD 104 and terminate at the target area of the body 108.

The patient 108 ultimately wants the IMD 104 to be recharged so that medical therapy can continue. The external device 102 may provide various functions including a recharge function whereby a recharge session is established between the external device 102 and the IMD 104. During the recharge session, recharge energy is provided while a far field telemetry communication session is also conducted to allow the external device 102 to receive feedback about charging status from the IMD 104 as well as for other purposes in some embodiments such as for programming the IMD 104 during the recharge session.

The external device 102 ultimately communicates with the IMD 104 during a recharge session through a far field telemetry communication session utilizing far field signals 114 sent by the external device 102 and far field signals 116 sent by the IMD 104. These far field signals 114, 116 may be radio frequency (RF) signals such as those of the Medical Implant Communications Service (MICS) band, the Industrial, Scientific, and Medical (ISM) band, or the short range device (SRD) band. The far field telemetry communication session may be used for additional purposes during the recharge session as discussed below. Far field telemetry communications are those where a wave, i.e., via an E-field, is propagated and that wave may be used to carry the communications as opposed to relying on an inductive coupling, i.e., via an H-field.

While the single IMD 104 is shown in FIG. 1, it will be appreciated that there may be other IMDs and/or other external devices nearby and in range of the far field signals 114 of the external device 102. In some embodiments, the external device 102 may or may not be aware of identification information of the intended IMD 104 in advance such that the external device 102 cannot immediately discern far field telemetry communications of the intended IMD 104 relative to far field telemetry communications of other IMDs. However, physical proximity can be established to allow proximity communication 112 and/or recharge energy transfer 120 to occur between the external device 102 and the intended IMD 104. Physical proximity refers to the intended IMD 104 being positioned closely to the external device 102 to the extent that an observer such as a clinician can confirm that the intended IMD 104 is the only IMD that can be responsive to proximity communications. Where the proximity communication is a signal from proximity telemetry, the proximity telemetry communications are those where the signal is typically an inductively coupled signal transfer, i.e., via an H-field. For proximity telemetry, the external device 102 must be within physical proximity of the IMD (i.e., within the patient's "personal space") for the IMD to communicate with the external device. This is opposed to far field communications wherein external device 102 may, but need not, be within physical proximity of the IMD to communicate with the IMD.

Therefore, a procedure is provided that utilizes this physical proximity at the initiation of the far field telemetry communication session and related recharge session to avoid the external device 102 conducting a far field telemetry communication session with an unintended nearby IMD while recharging the intended IMD 104. To allow the external device 102 to select the intended IMD 104 for far field telemetry communication during a recharge session and avoid selecting an unintended nearby IMD, proximity communication signals 112 may be exchanged between a proximity communicator 110 and the IMD 104 during the establishment of the far field telemetry communication session.

The proximity communicator 110 may be of various forms and may be a separate component of the external device 102 or be integrated with the external device 102, or a combination of both. For instance, the proximity communicator 110 may be a near field telemetry head that is tethered to the external device 102 by a communication path 118 such as a cable or wireless connection and that establishes an inductive link with the IMD 104. The proximity communicator 110 may utilize the transfer of recharge energy as a proximity communication. As another example, the proximity communicator 110 may be an audible tone generator where the IMD 104 receives and recognizes different audible tones. As another example, the proximity communicator 110 may be a body thump device, such as a chest thump device, where the IMD 104 detects the thump through an on-board accelerometer or other vibration detector. As yet another example, the proximity communicator 110 may be a static field generating device such as an electromagnet or a permanent magnet being moved into and out of proximity with the IMD 104 by the clinician.

In some cases including the near field telemetry head, the audible signal generator, the body thump device, and the electromagnet, the proximity communicator 110 may be under control of the external device 102 through a tethered or wireless connection between the telemetry head 110 and the external device 102. In some cases including the clinician providing the body thump or moving the permanent magnet, the proximity communicator 110 is under direct control of the clinician who may be following commands being issued by the external device 102 to provide or remove the proximity communication.

The proximity communicator 110 may also integrate recharge circuitry including a recharge coil that inductively couples to a coil of the IMD 104 to inductively transfer energy. Thus, a single tool may be placed in physical proximity of the patient 108 in order to establish a form of proximity communication and to delivery recharge energy. Where the connection 118 is wired, recharge energy may be sourced from the external device 102. Where the connection 118 is wireless, the recharge energy may be sourced from an on-board power supply of the proximity communicator 110. As an alternative, the recharge device may be a separate device from the proximity communicator 110 where both are held in physical proximity to the patient 108 and linked to the external device 102.

The proximity communication may range from being a simple present or absent signal to a more complex signal carrying data. Furthermore, the proximity communication may be a unidirectional communication mode in some embodiments, particularly where the communication is simple. This may reduce the cost and complexity of a device, particularly the IMD 104. One particular example of proximity communication may be the presence or absence of recharge energy, and this recharge energy may be pulsed in accordance with a particular pattern that the IMD 104 may discern and which the IMD 104 may echo back to the external device 102. The proximity communication may be a bi-directional communication mode in other embodiments, such as where one device may send data through a proximity communication while the other device may send an acknowledgement through a subsequent proximity communication. This may improve the efficiency of the proximity communication procedure.

Figure 2:
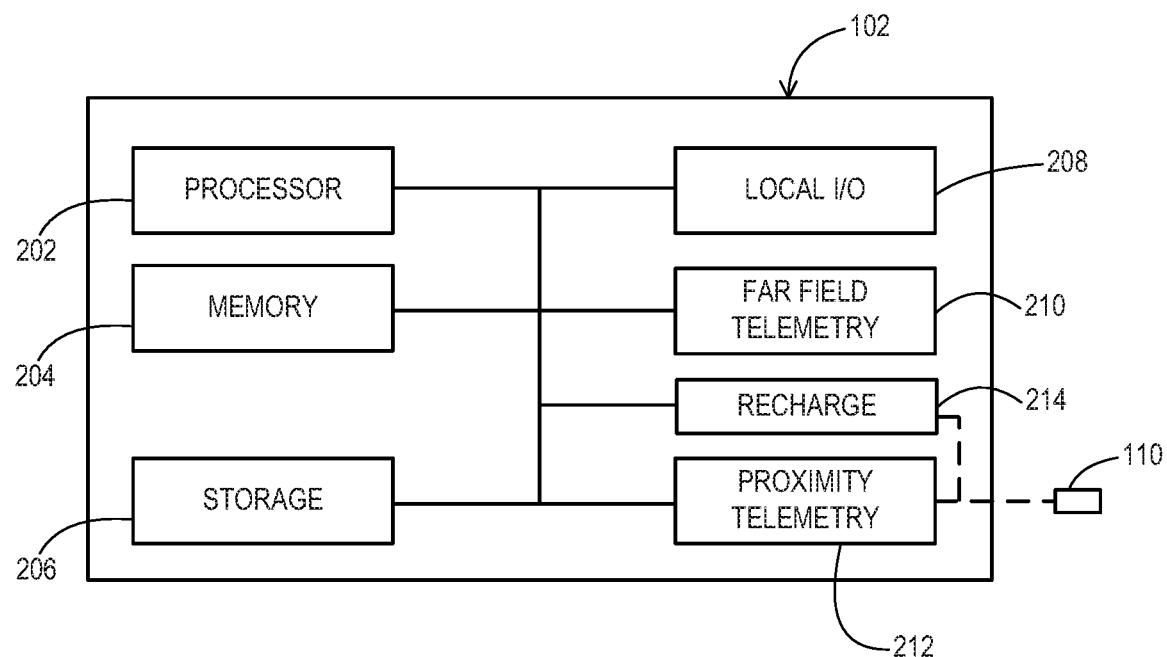
FIG. 2 shows an example of components of an external device of the medical system.

FIG. 2 shows components of one example of the external device 102. The external device 102 includes a processor 202, a memory 204, and a storage device 206. The external device 102 may also include local input/output (I/O) ports 208 such as to provide local screen displays and to receive user input via keyboard, mouse, and so forth. The external device 102 also includes far field telemetry communication circuitry 210 used to establish the far field telemetry communication session with the IMD 104. The far field telemetry communication circuitry 210 may drive a signal propagation tool such as an RF antenna. The signal propagation tool may be included within the proximity communicator 110 so that the far field telemetry communication circuitry 210 instructs the signal propagation tool over the connection 118 or the signal propagation tool may be a separate external component or housed within the external device 102.

In addition to the far field telemetry communication circuitry 210, the external device 102 also includes proximity telemetry communication circuitry 212. The proximity telemetry communication circuitry 212 may be of various forms to interact with the proximity communicator 110. The link between the proximity telemetry communication circuitry 212 and the proximity communicator 110 may be a wired or wireless connection, for example using universal serial bus protocol, Bluetooth® protocol, or other such protocols, that provides data commands to circuitry within the proximity communicator 110 to produce the proximity communication signal. The proximity communicator 110 may then include a near field inductive driver circuit, a signal generator for producing audible tones, a motion signal generator for driving a body thump device, a field producing circuit for driving an electromagnet, and the like that are responsive to the data commands. Alternatively for a wired connection, these circuits may be included in the proximity telemetry communication circuitry 212 to drive the proximity communicator 110 directly.

The external device 102 may include additional communication capabilities that may be provided by far field telemetry communication circuitry 210 or by additional communication circuitry. For instance, the external device 102 may include Wi-Fi connectivity, public switched telephone network connectivity, and so forth to allow for remote communication, particularly where the external device 102 is a patient controlled device.

The external device 102 may include a recharge circuit 214 that generates recharge waveforms to inductively transfer energy to the IMD 104. The recharge circuit 214, for example, may include a coil that is driven by a waveform generator that receives energy from a power supply. The recharge circuit 214 may utilize the coil that may be present within the proximity communicator 110 to deliver the recharge energy.

The memory 204 may be used to store information in use by the processor 202. For instance, the memory 204 may store therapy parameters that are input by a clinician or patient that are to be loaded into the IMD 104. The memory 204 may also store programming that is used by the processor 202 to control the IMD selection procedure of the external device 102, to control the delivery of the recharge energy, and/or to control periodically suspending the far field telemetry communication session while the transfer of power continues. The memory 204 may be of various types, such as volatile, non-volatile, or a combination of the two.

The storage device 206 may be used to store information for a long term and may be of various types such as non-volatile so that the information is retained when the external device 102 is powered off. The storage device 206 may also store programming for the processor 202 that is implemented to control the IMD selection procedure, the delivery of recharge energy, and the periodic suspension of the far field telemetry communication session while the power continues to be transferred. Examples of the storage device 206 include electronic, magnetic, and optical drives including fixed and removable types such as secure digital cards and the like. The storage device 206 and the memory 204 are both examples of computer readable media that may store information in the form of computer programming, data structures, and the like.

Figure 4A:
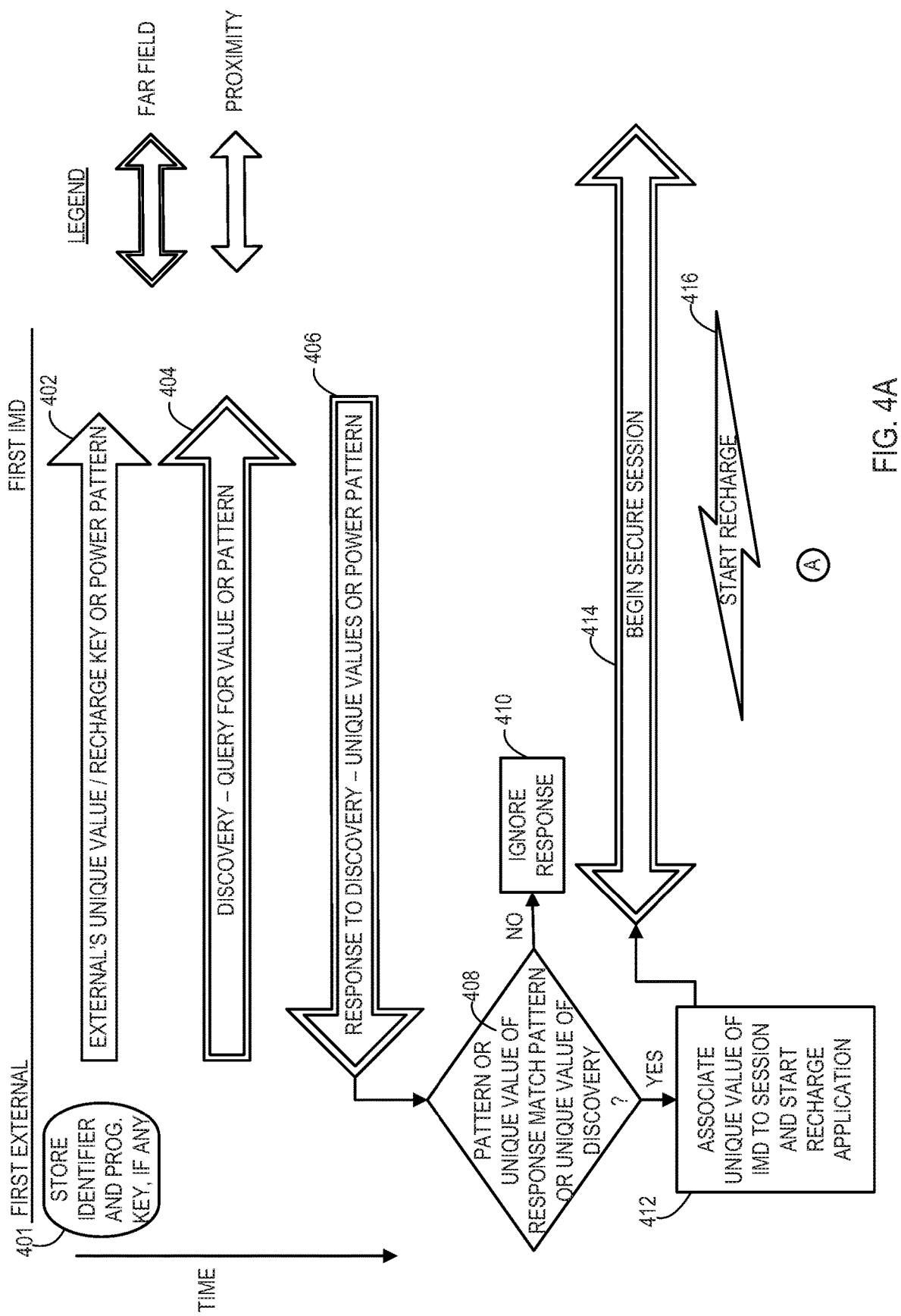
FIGS. 4A-4C show examples of operations of the external device and the implantable medical device of a medical system.
Figure 4B:
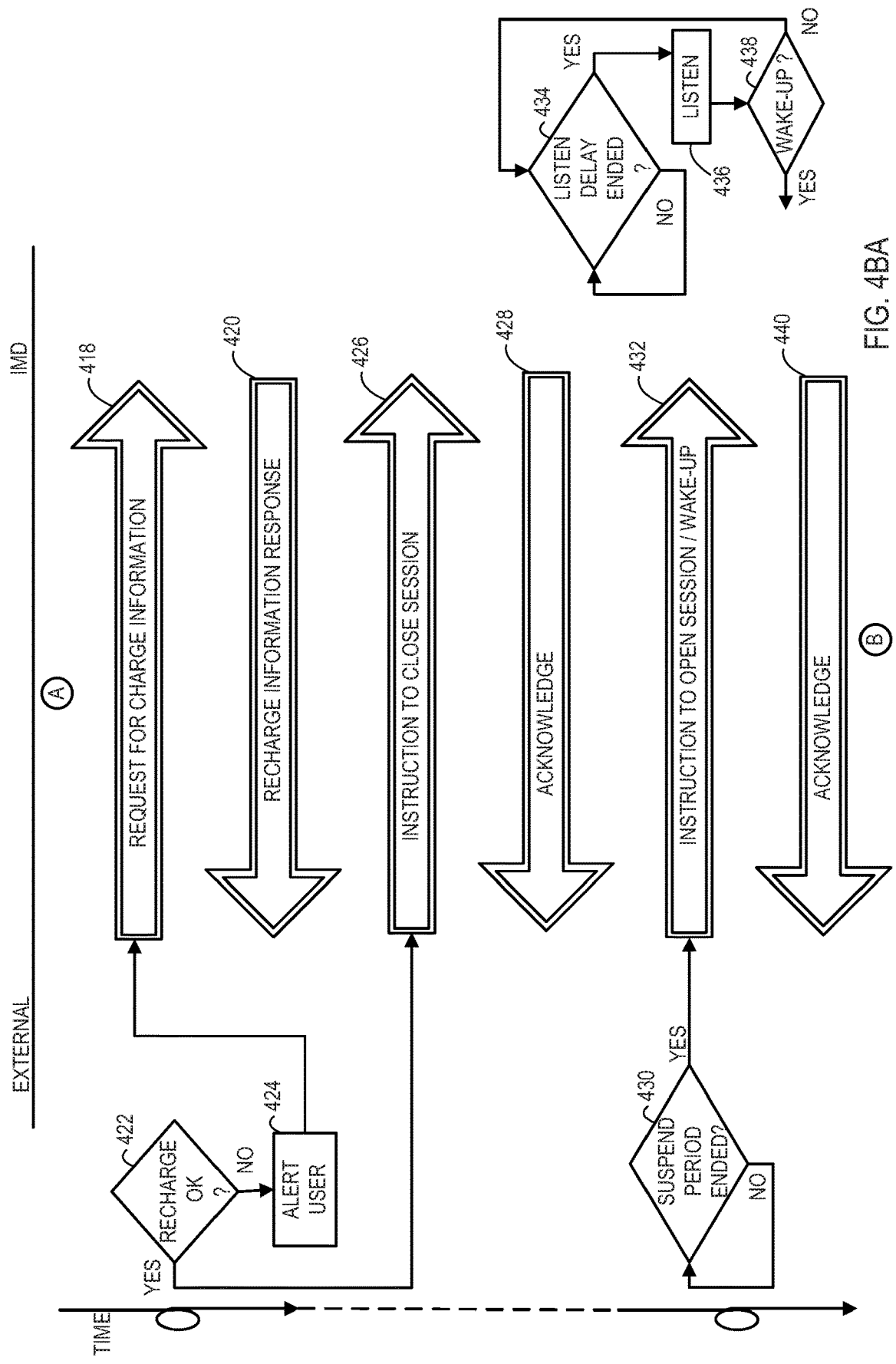
Figure 4B:
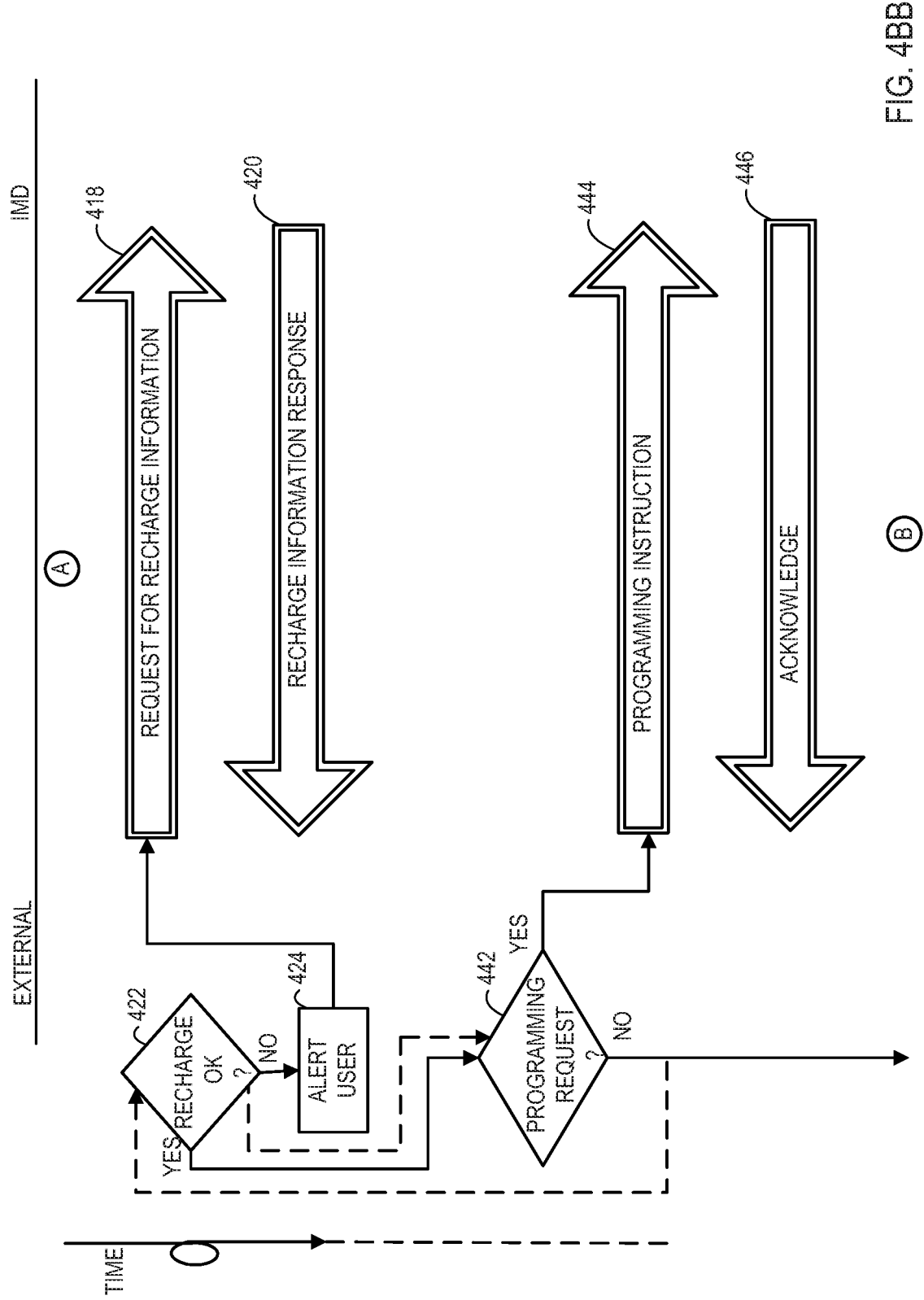
Figure 4C:
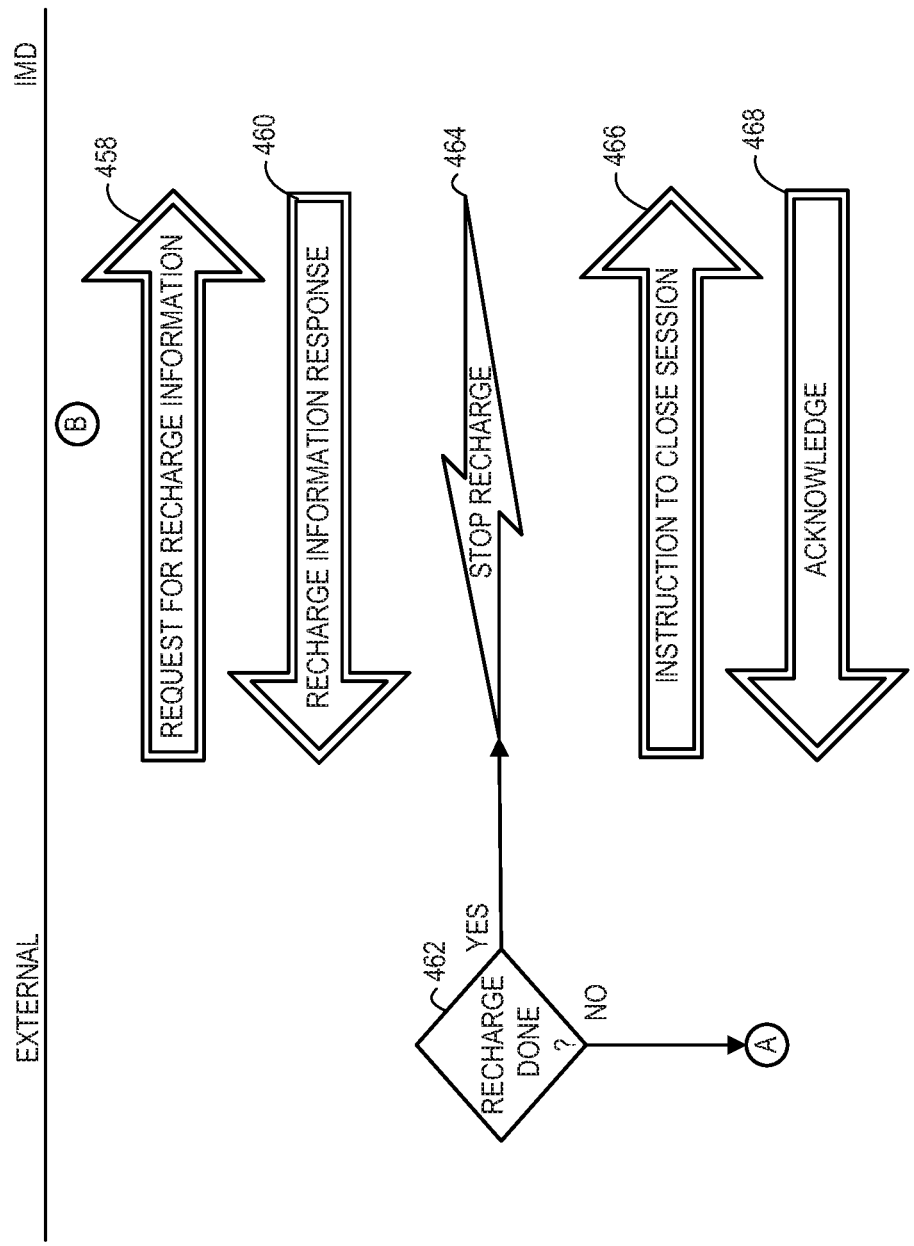

The processor 202 performs logical operations to provide a sequence of far field and proximity communications, to control delivery of recharge energy, to control the far field telemetry communications and periodic suspension, and to make related decisions such as those of FIGS. 4A-4C to allow far field telemetry communication sessions with the IMD 104 to be established in conjunction with a recharge session. The processor 202 may be of various forms. For instance, the processor 202 may be a general-purpose programmable processor that executes software that is stored on the storage device 206 or elsewhere. Other examples include a dedicated purpose hardware circuit or hard-wired digital logic. The processor 202 may be multiple separate components or processors, dedicated hardware/state machine, and the like. The processor 202 may communicate with the various other components through one or more data buses.

Figure 3:
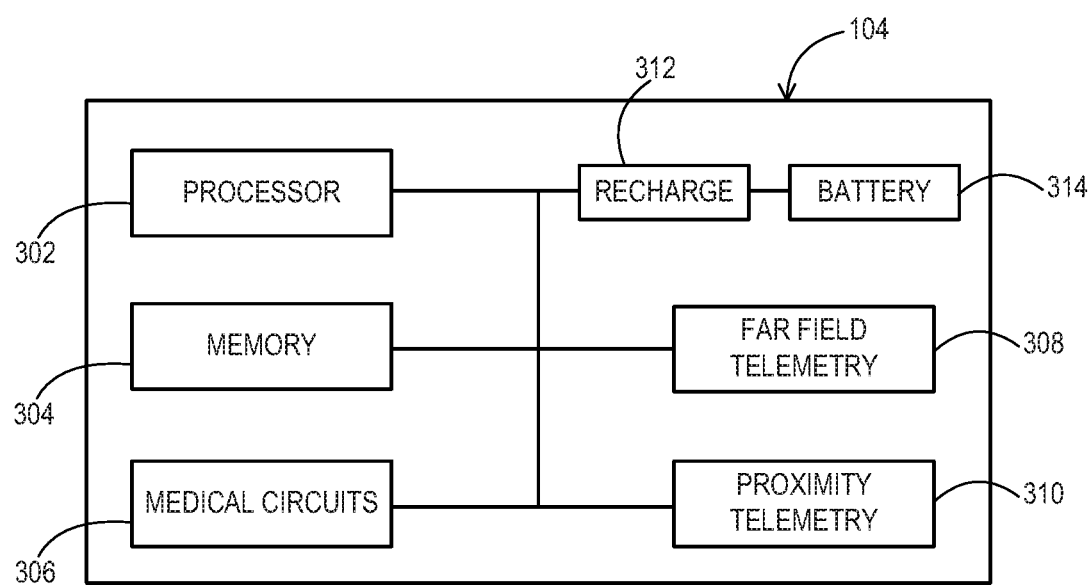
FIG. 3 shows an example of components of an implantable medical device of the medical system.

FIG. 3 shows components of one example of the IMD 104 to be recharged. The IMD 104 includes a processor 302 and a memory 304. The IMD 104 also includes medical circuitry 306 that performs a medical task such as stimulation, drug delivery, monitoring, and the like. The IMD 104 also includes far field telemetry communication circuitry 308 used to establish the far field telemetry communication session with the external device 102 independently of or in conjunction with a recharge session. The far field telemetry communication circuitry 308 may drive a signal propagation tool such as an integral RF antenna.

In addition to the far field telemetry communication circuitry 308, the IMD 104 also includes proximity communication circuitry 310. The proximity telemetry communication circuitry 310 may be of various forms where for a given system, the type of proximity telemetry communication circuitry 310 matches the type of proximity communicator 110 that the external device 102 includes. Accordingly, the proximity telemetry communication circuitry 310 may be a near field inductive receiver, a microphone for receiving audible tones, an accelerometer or other vibration detection device, a field operable switch such as a magnetic reed switch, and the like.

The IMD 104 also includes a rechargeable battery 314 and a recharge circuit 312 coupled to the battery 314. The recharge circuit 312 may include a coil that inductively couples to the coil of the recharge circuit 214 of the external device 102. The recharge circuit 312 may utilize a dedicated coil or may utilize a coil that is also used by the proximity telemetry communication circuit 310. The recharge circuit 312 may include rectification, filtering, voltage/current limiting, and the like so as to provide an appropriate form of recharge power to the battery 314.

The memory 304 may be used to store information in use by the processor 302 such as programming and data values. The memory 304 may store additional information including therapy parameters that are used to control the medical circuitry 306 as well as recharge parameters that are used to control the recharge circuitry 312. The memory 304 may be of various types such as volatile, non-volatile, or a combination of the two. The memory 304 is also an example of computer readable media that may store information in the form of computer programming, data structures, and the like.

The processor 302 performs logical operations to provide a sequence of far field and proximity communications, to control delivery of recharge energy, to cooperate with the periodic suspension of the far field telemetry communication session while the power continues to be transferred, and to make related decisions such as those of FIGS. 4A-4C to allow far field telemetry communication sessions with the external device 102 to be established independently of and in conjunction with a recharge session. The processor 302 may be of various forms like those discussed above for the processor 202 of the external device 102 and as discussed above may be multiple separate components or processors, dedicated hardware/state machine, and the like. The processor 302 may communicate with the various other components through one or more data buses.

FIG. 4A describes proximity based communications being used to facilitate far field recharge sessions in conjunction with recharge or status sessions. While this example shows proximity communications being directed from an external device 102 to an IMD 104, it will be appreciated that in some cases the roles may be reversed and the direction of the proximity communications may be reversed whereby the IMD 104 may send proximity communications rather than or in addition to the external device 102 doing so.

FIG. 4A shows a first example of a procedure to establish a far field telemetry communication session where a unique value and/or key are shared via a proximity communication. The proximity communication may be of a type that can carry data or may be a presence, absence, or pattern of recharge energy. Furthermore, the proximity communication may be bi-directional so that an acknowledgement may be returned as a confirmation of receipt of the data so that a successful initial data transfer via the proximity communication can be completed as a prerequisite to attempting subsequent steps.

Initially, the external device 102 may store an identifier of a program bonded IMD and may also store a programming key for that bonded IMD as indicated at state 401. For security, some embodiments may preclude far field telemetry communication between external devices 102 and IMDs 104 unless the two are bonded, and utilizing the proximity communication is an example of bonding the two including sharing identifiers and/or programming keys. The identifier and programming key allows the external device 102 to conduct a far field programming session without requiring a proximity communication to occur between the external device and the IMD where the two have already been bonded and where a programming session is being conducted. Thus for any given far field session, the programming key and identifier may have previously been exchanged by virtue of a proximity based process.

In FIG. 4A, a recharge session is desired between the first external device 102 and the first IMD 104 to be recharged. In this particular example, because the user has selected to conduct a recharge session via the external device, the bond that the external device 102 may have, if any, is not applicable to initiating a far field telemetry communication session in conjunction with a recharge session. Exchanging a recharge key to be used for far field telemetry communications during recharge via the proximity communications and allowing the key to expire at the conclusion of the recharge session creates a temporary bond between the external device 102 and the IMD 104 to be recharged for purposes of conducting far field telemetry communications during a recharge session with an IMD 104 to be recharged. This may be useful, for instance, where an external device of a clinician that has not been bonded to the IMD 104 is being used to conduct the recharge session. In some embodiments, even where an external device 102 of the patient having the IMD 104 is bonded to the IMD 104 being recharged, a temporary bond via a recharge key may be created. In other embodiments where the external device 102 of the patient having the IMD 104 is bonded to the IMD 104, the recharge session and related far field telemetry communication session may begin by utilizing the previously exchanged program key rather than exchanging a temporary recharge key.

The recharge session may be initiated in various ways according to various embodiments. For instance, the external device 102 may present a menu option to a user for beginning a recharge session. As another example, the external device 102 may prompt the user as to whether to begin recharge in response to some event, such as the user plugging in a recharge tool such as the proximity communicator 110 into the external device. As yet another example, the external device 102 may begin the recharge session automatically in response to some event, such as the user plugging in a recharge tool such as the proximity communicator 110 in to the external device.

Initially, for embodiments where a bond does not exist or where a bond is not used for far field telemetry communications during a recharge session, the external device 102 may send a proximity communication 402 that includes a value that is unique to the external device 102 to the IMD 104. For example, the unique value may be a device serial number, hardware identification number, randomly generated number, a security key value, a combination, or other such values that may be unique to the external device 102. As another example, the proximity communication 402 may be recharge energy that may be constant, pulsed, or otherwise manipulated so as to be unique. Because this information is transferred through the proximity communication 402, no other nearby IMD will receive this information or pattern of recharge energy. The external device 102 also sends a far field discovery communication 404 shortly before, during, or shortly after sending the proximity communication 402. The IMD 104 as well as other nearby IMDs may receive and respond to this far field discovery communication 404.

In one example, the IMD 104 may respond only to a discovery request that is within a certain time of receiving the proximity communication 402, such as a simultaneous occurrence of the proximity communication 402 and the discovery communication 404 or within a predefined delay from one to the next. In this example, the IMD 104 and potentially other nearby IMDs as well are configured to respond by sending the unique value that each has received via a proximity communication and also by sending a value that is unique to the IMD. For example, this value may be a device serial number, hardware identification number, randomly generated number, a security key value, a combination, or other such values that may be unique to the IMD 104.

Only the far field response communication 406 from the IMD 104 of interest will have the unique value that corresponds to the external device 102. Other IMDs would either have no unique value of an external device to send or would send the unique value of a different external device. Furthermore, in some examples, only those IMDs that receive the discovery communication 404 within a specified time relative to a proximity communication, such as the proximity communication 402 received by the intended IMD 104, bother to respond with a far field response communication such as the far field response communication 406 from the intended IMD 104.

For each far field response communication, the external device 102 attempts to verify the shared unique value by determining whether the unique value being received matches the unique value that was previously sent over the proximity communication 402 at a query operation 408. If a particular response does not include a matching value, then that particular response is ignored at operation 410.

For embodiments using processes such as those of FIG. 4A where discovery via far field telemetry communications is attempted, the external device 102 and IMDs may be configured to apply collision avoidance and backoff algorithms. These algorithms allow devices to re-attempt to send and/or receive expected far field telemetry communications where two devices may attempt to send a far field telemetry communication at the same time such that neither transmission is received and acknowledged. A re-attempt to send the far field telemetry communication occurs by each of the sending devices but at different times on the second attempts because the backoff algorithm of each sending device randomly chooses the time for the re-attempt. This reduces the likelihood of collisions occurring multiple times. Thus, the external device 102 eventually receives a discovery response that has not collided with another. Furthermore, the external device 102 eventually receives a discovery response from the IMD 104 for which proximity communication 402 has been established.

For the response 406 which does have the matching unique value from the proximity communication 402, the external device 102 then associates the value that is unique to the IMD 104 and that is included in the far field response communication 406 to the far field telemetry communication session being established at an association operation 412. The external device 102 may also then execute the appropriate recharge program automatically based on the value that is unique to the IMD 104 where the external device 102 stores associations of such values to recharge applications.

The external device 102 then begins the far field telemetry communication session 414 and the related recharge session 416 with the IMD 104. The external device 102 may communicate during the far field session 414 by using the unique value of the external device 102 of which the IMD 104 is aware to identify the sender of transmissions and/or using the unique value of the IMD 104 to identify the intended recipient of transmissions. Likewise, the IMD may communicate during the far field session 414 by using the unique value of the IMD 104 of which the external device 102 is aware to identify the sender of transmissions and/or using the unique value of the external device 102 to identify the intended recipient of transmissions.

The far field session 414 may be made secure by encrypting the information with an encryption key, such as the recharge key when a temporary bond has been created or the program key where a permanent bond has been previously created and is now being used. In the case of a temporary bond for the recharge session, the recharge key may have been generated for the session by the external device 102 and included in the proximity communication 402 so that the IMD 104 already has the key. Alternatively, the key may be exchanged in another manner and/or at another time in the sequence such as by using a low power radio frequency communication to minimize the range and thereby provide a level of security for the transfer of the recharge key to the IMD 104. Furthermore, the IMD 104 may provide the recharge key for the secure far field session 414 rather than receiving the key from the external device 102.

During the far field session 414, recharge information may be exchanged between the IMD 104 being recharged and the external device 102 that is in control of recharging the IMD 104. This recharge information may include diagnostic information that allows the external device 102 to monitor the recharge efficiency, the status of the battery, and the like. The external device 102 may control the delivery of the recharge energy 416 in response to such diagnostic information such as by increasing or decreasing the level of recharge energy 416, prompting the user to adjust the position of the recharge tool, and to eventually terminate the recharge session upon detection of a fully recharged battery 314. The exchange of recharge information via far field telemetry communications occurs simultaneously with the delivery of the recharge energy as a result of the far field telemetry communications being significantly out-of-band relative to the recharge energy waveform.

After starting the recharge energy 416, operational flow then carries on with further interaction between the external device 102 and the IMD 104. Examples of these further interactions are set forth in the alternative operations of FIG. 4BA, 4BB, 4BCA-4BCB, or 4BDA-4BDB, while the operational flow then concludes in FIG. 4C.

FIG. 4BA shows a first option for operations of the external device 102 and the IMD 104. Here, the external device 102 sends a far field telemetry communication 418 that requests the recharge information. The IMD 104 responds with a far field telemetry communication 420 that includes the recharge information. The recharge information may include diagnostic information noted above which may include values such as a tally of Coulombs received since a previous request for recharge information which indicates current recharge efficiency as well as an impedance, a voltage, or other value that is representative of the status of the battery.

Upon receiving the recharge information, the external device 102 then detects at a query operation 422 whether the recharge process has an acceptable efficiency based on whether an adequate number of Coulombs were received since the previous request for recharge information. If the charging efficiency is inadequate, then the external device 102 then generates an alert to the user at an alert operation 424. The alert indicates to the user that the proximity communicator/recharge head 110 needs to be re-positioned closer to the IMD 104. The external device 102 then begins repeatedly requesting recharge information at intervals while maintaining the far field telemetry communication session in an open state and maintaining the alert. The external device 102 detects from each response 420 whether the Coulomb count has reached a level indicative of adequate charging efficiency.

In each of the options shown in FIGS. 4BA, 4BB, 4BCA-4BCB, and 4BDA-4BDB, the external device 102 may also monitor the recharge circuit 214 to detect changes in the coupling between the coil of the recharge circuit 214 and the coil of the recharge circuit 312 of the IMD 104. Detecting a change in the coupling of the coils may also indicate that there may be a problem with the position. The external device 102 may utilize the detection of this change together with the Coulomb count to confirm that the position of the recharge head 110 does need to be changed. The detection of the change in the coupling may be done at the time of analyzing the diagnostic information including the Coulomb count received from the IMD 104 at the query operation 422. Furthermore, the external device 102 may utilize the detected change in the coupling that may occur during a suspension period when the far field telemetry communication session is temporarily closed to trigger an early end to the suspension period, which is discussed below in relation to a query operation 430. This early end to the suspension period would allow the external device 102 to more quickly obtain the diagnostic information from the IMD 104.

Upon the external device 102 detecting that the charging efficiency is adequate, the external device 102 stops generating the alert and then sends an instruction 426 to the IMD 104 to close the communication session. The IMD 104 then sends an acknowledgement 428 and deactivates the far field telemetry communication circuitry 308. For instance, to the extent the far field telemetry communication circuitry 308 is a standalone module, the entire module may be powered down. To the extent the far field telemetry communication circuitry is combined with other functional elements within a common module, the far field telemetry communication circuitry 308 portion of the module may be powered down. This begins the suspension period during which time the far field telemetry communications are stopped. To the extent the IMD 104 has separate processing for controlling the far field telemetry communications, this processing may also be deactivated during the suspension period to further conserve energy such as by entering a sleep state or otherwise being powered down as well. Such deactivation related to the far field telemetry communications may provide significant energy savings during recharge and thereby reduce the length of the recharge process. It has been observed that in some cases the reduction in the length of the recharge period due to this deactivation may approach ten percent or more.

The IMD 104 then begins detecting whether a listen delay period which sets the interval between attempts to briefly to listen for a wake-up signal from the external device 102 has ended. When the period of delay has ended, the IMD 104 then activates the far field telemetry communication circuitry 308 to briefly listen for a wake-up signal from the external device 102 at a listen operation 436. In this example, the IMD 104 may listen for a few milliseconds. The IMD 104 detects whether the wake-up signal has been received at a query operation 438. If a wake-up signal has not been received, the IMD 104 deactivates the far field telemetry communication circuitry 308 and restarts the listen delay period at query operation 434 to delay until the next listen attempt.

Meanwhile, the external device 102 is detecting whether the suspension period noted above for the far field telemetry communication session has expired at a query operation 430. The suspension period may be at least as lengthy as the listen delay period for the IMD 104 and in some embodiments may be significantly longer. For instance, the listen delay period may be less than 1 second which ensures the IMD 104 can quickly enter into far field telemetry communications. The suspension period of the external device 102 during a recharge session may be significantly longer, for instance from 10 seconds to a minute or more, which significantly reduces the amount of energy expended by the IMD 104 in comparison to leaving the far field telemetry communication session open for the entire recharge session. Thus, lengthening the suspension period helps to shorten the time required to complete the recharge process.

Once the suspension period has ended, the external device 102 then sends a wake-up instruction 432 to open the far field telemetry communication session. This instruction 432 is sent at a time when the IMD 104 should be listening at an instance of the listen operation 436. The IMD 104 sends an acknowledgement 440 after receiving the wake-up instruction 432. If the external device 102 does not receive an acknowledgement 440 immediately after sending the wake-up instruction 432, the external device 102 may repeat the wake-up instruction 432 until the acknowledgement 440 is received.

The key being used to encrypt and decrypt the far field messages may be either a permanent key such as a programming key or a temporary key such as a recharge key dedicated for one particular recharge session. In the case of a temporary key, the key may have an expiration. However, where the expiration period is computed based on the time from the last far field telemetry communication, the expiration value of the temporary key is longer than the suspension period and is therefore still valid at each point in time when the external device 102 attempts to wake-up the IMD 104 during a given recharge session. Where the expiration period of a temporary key is computed based on the time from the first far field telemetry communication, the expiration value of the temporary key is longer than the recharge session itself and is therefore still valid at each point in time when the external device 102 attempts to wake-up the IMD 104 during a given recharge session.

Upon the acknowledgement 440 being received in FIG. 4BA, operational flow then proceeds to FIG. 4C where the external device sends a request 458 for recharge information and the IMD 104 provides a response 460. The external device 102 detects from the recharge information whether the battery is fully recharged at a query operation 462. For instance, the external device 102 may detect whether an impedance or voltage of the battery 314 has increased to a level indicative of a full charge. If the battery is fully recharged, then the external device stops the transfer of power for recharge at state 464. Then, the external device 102 sends an instruction 466 to close the session for the final time, and the IMD 104 sends an acknowledgement 468 for the final time. If the battery is not full, then the external device repeats the operations of FIG. BA, where the request 418 may be sent after closing the communication session and delaying for another suspension period.

FIG. 4BB shows a second option for operations of the external device 102 and the IMD 104 after the conclusion of the operations of FIG. 4A. Here, the external device 102 sends a far field telemetry communication 418 that requests the recharge information. The IMD 104 responds with a far field telemetry communication 420 that includes the recharge information.

Upon receiving the recharge information, the external device 102 then detects at a query operation 422 whether the recharge process has an acceptable efficiency based on whether an adequate number of Coulombs were received since the previous request for recharge information. If the charging efficiency is inadequate, then the external device 102 then generates an alert to the user at an alert operation 424. The alert indicates to the user that the proximity communicator/recharge head 110 needs to be re-positioned closer to the IMD 104. The external device 102 then begins repeatedly requesting recharge information at intervals while maintaining the far field telemetry communication session in an open state and maintaining the alert. The external device 102 detects from each response 420 whether the Coulomb count has reached a level indicative of adequate charging efficiency.

According to some embodiments implementing the option of FIG. 4BB, while repeatedly requesting recharge information in order to monitor whether the re-positioning of the recharge head 110 is improving the recharge efficiency, the external device 102 may also be monitoring for a programming request from a user at a query operation 442. When a programming request is received, the external device may interleave a programming instruction 444 with the requests for recharge information, where the IMD 104 responds to the programming instruction 444 with an acknowledgement. Alternatively, the external device 102 may queue the programming instruction and then send the programming instruction 444 upon determining at the query operation 422 that the recharge efficiency has returned to normal levels.

Additionally, upon the external device 102 detecting that the charging efficiency is adequate, the external device 102 stops generating the alert and then may again detect at the query operation 442 whether a programming request has been received from a user of the external device 102. If a programming request is received, then the external device 102 sends a far field telemetry communication containing the programming instruction 444. The IMD 104 then responds with the acknowledgement 446. In each of the options discussed herein for FIGS. 4BB through 4BDB that involve sending programming instructions, the far field telemetry communication that contains the programming instruction may be encrypted with a key, such as a permanent programming key or a temporary key such as the recharge key that is dedicated to the recharge session, that has been previously shared between the external device 102 and the IMD 104, such as by a proximity communication or a low power far field telemetry communication.

Additionally, upon the external device 102 detecting that the charging efficiency is adequate, the external device 102 stops generating the alert and then may again detect at a query operation 442 whether a programming request has been received from a user of the external device 102. If a programming request is received, then the external device 102 sends a far field telemetry communication containing the programming instruction 444. The IMD 104 responds to the programming instruction 444 with the acknowledgement 446.

Operational flow then transitions to FIG. 4C where the operations continue as discussed above. If a programming request is not received, then operational flow transitions directly from the query operation 442 to the operations of FIG. 4C that continue as discussed above.

FIGS. 4BCA-4BCB show a third option for operations of the external device 102 and the IMD 104 after the conclusion of the operations of FIG. 4A. Here, the external device 102 sends a far field telemetry communication 418 that requests the recharge information. The IMD 104 responds with a far field telemetry communication 420 that includes the recharge information.

Upon receiving the recharge information, the external device 102 then detects at a query operation 422 whether the recharge process has an acceptable efficiency based on whether an adequate number of Coulombs were received since the previous request for recharge information. If the charging efficiency is inadequate, then the external device 102 then generates an alert to the user at an alert operation 424. The alert indicates to the user that the proximity communicator/recharge head 110 needs to be re-positioned closer to the IMD 104. The external device 102 then begins repeatedly requesting recharge information at intervals while maintaining the far field telemetry communication session in an open state and maintaining the alert. The external device 102 detects from each response 420 whether the Coulomb count has reached a level indicative of adequate charging efficiency.

According to some embodiments implementing the option of FIGS. 4BCA-4BCB, while repeatedly requesting recharge information in order to monitor whether the re-positioning of the recharge head 110 is improving the recharge efficiency, the external device 102 may also be monitoring for a programming request from a user at a query operation 442. When a programming request is received, the external device may interleave a programming instruction 444 with the requests for recharge information, where the IMD 104 responds to the programming instruction 444 with an acknowledgement. Alternatively, the external device 102 may queue the programming instruction and then send the programming instruction 444 upon determining at the query operation 422 that the recharge efficiency has returned to normal levels.

Additionally, upon the external device 102 detecting that the charging efficiency is adequate, the external device 102 stops generating the alert and then may again detect at the query operation 442 whether a programming request has been received from a user of the external device 102. If a programming request is received, then the external device 102 sends a far field telemetry communication containing the programming instruction 444. The IMD 104 then responds with the acknowledgement 446.

Where a programming request has not been received at the query operation 442, or where the acknowledgement 446 of a programming instruction 444 has been received, the external device 102 then sends an instruction 426 to the IMD 104 to close the communication session. The IMD 104 then sends an acknowledgement 428 and deactivates the far field telemetry communication circuitry 308 such as by powering down. As noted above, to the extent the IMD 104 has separate processing for controlling the far field telemetry communications, this processing may also be deactivated to further conserve energy such as by entering a sleep state.

The external device 102 then begins detecting whether a programming request has been received from a user at a query operation 448 and whether the suspension period has ended at a query operation 430. Meanwhile, the IMD 104 begins detecting whether the listen delay period has ended at query operation 434. Where a programming request is received, then rather than waiting for the end of the suspension period, the external device 102 proceeds to send a wake-up instruction 431 to open the far field telemetry communication session. This instruction 431 is sent at a time when the IMD 104 should be listening at an instance of the listen operation 436. The IMD 104 sends an acknowledgement 441 after receiving the wake-up instruction 431. If the external device 102 does not receive an acknowledgement 441 immediately after sending the wake-up instruction 431, the external device 102 may repeat the wake-up instruction 431 until the acknowledgement 441 is received.

Upon receiving the acknowledgement 441, the external device 102 then sends the programming instruction 450. The IMD 104 then sends an acknowledgement 452. The external device 102 then proceeds to send an instruction 427 to close the far field session. The IMD 104 then sends an acknowledgement 429.

Upon the suspension period ending at the query operation 430, the external device 102 then sends a wake-up instruction 432 to open the far field telemetry communication session. This instruction 432 is sent at a time when the IMD 104 should be listening at an instance of the listen operation 436. The IMD 104 sends an acknowledgement 440 after receiving the wake-up instruction 432. If the external device 102 does not receive an acknowledgement 440 immediately after sending the wake-up instruction 432, the external device 102 may repeat the wake-up instruction 432 until the acknowledgement 440 is received. Operational flow then proceeds to FIG. 4C and continues as discussed above.

While the external device 102 is detecting whether a programming request has been received at the query operation 448 and whether the suspension period has ended at the query operation 430, the IMD 104 is detecting whether the listen delay period has ended at the query operation 434. When the period of delay has ended, the IMD 104 then activates the far field telemetry communication circuitry 308 to briefly listen for a wake-up signal from the external device 102 at the listen operation 436. The IMD 104 detects whether the wake-up signal has been received at the query operation 438. If a wake-up signal has not been received, the IMD 104 deactivates the far field telemetry communication circuitry 308 and restarts the listen delay period at query operation 434 to delay until the next listen attempt. Where the wake-up signal has been received, the IMD 104 provides the acknowledgement 440 or 441.

FIGS. 4BDA-4BDB show a fourth option for operations of the external device 102 and the IMD 104 after the conclusion of the operations of FIG. 4A. In this option, there may be less urgency for sending the programming instruction, or the suspension period may be relatively small, such as on the order of a few seconds, so that the delay in sending the programming instruction is minor. Here, the external device 102 sends a far field telemetry communication 418 that requests the recharge information. The IMD 104 responds with a far field telemetry communication 420 that includes the recharge information.

Upon receiving the recharge information, the external device 102 then detects at a query operation 422 whether the recharge process has an acceptable efficiency based on whether an adequate number of Coulombs were received since the previous request for recharge information. If the charging efficiency is inadequate, then the external device 102 then generates an alert to the user at an alert operation 424. The alert indicates to the user that the proximity communicator/recharge head 110 needs to be re-positioned closer to the IMD 104. The external device 102 then begins repeatedly requesting recharge information at intervals while maintaining the far field telemetry communication session in an open state and maintaining the alert. The external device 102 detects from each response 420 whether the Coulomb count has reached a level indicative of adequate charging efficiency.

According to some embodiments implementing the option of FIGS. 4BDA-4BDB, while repeatedly requesting recharge information in order to monitor whether the re-positioning of the recharge head 110 is improving the recharge efficiency, the external device 102 may also be monitoring for a programming request from a user at a query operation 442. When a programming request is received, the external device 102 may interleave a programming instruction 444 with the requests for recharge information, where the IMD 104 responds to the programming instruction 444 with an acknowledgement. Alternatively, the external device 102 may queue the programming instruction and then send the programming instruction 444 upon determining at the query operation 422 that the recharge efficiency has returned to normal levels.

Additionally, upon the external device 102 detecting that the charging efficiency is adequate, the external device 102 stops generating the alert and then may again detect at the query operation 442 whether a programming request has been received from a user of the external device 102. If a programming request is received, then the external device 102 sends a far field telemetry communication containing the programming instruction 444. The IMD 104 then responds with the acknowledgement 446.

Where a programming request has not been received at the query operation 442, or where the acknowledgement 446 of a programming instruction 444 has been received, the external device 102 then sends an instruction 426 to the IMD 104 to close the communication session. The IMD 104 then sends an acknowledgement 428 and deactivates the far field telemetry communication circuitry 308. As noted above, to the extent the IMD 104 has separate processing for controlling the far field telemetry communications, this processing may also be deactivated to further conserve energy.

The external device 102 then begins detecting whether a programming request has been received from a user at a query operation 448 and whether the suspension period has ended at a query operation 433. Meanwhile, the IMD 104 begins detecting whether the listen delay period has ended at query operation 434. Where a programming request is received, then rather than proceeding to send a wake-up instruction to open the far field telemetry communication session, the external device 102 waits for the end of the suspension period as detected at the query operation 433.

Upon reaching the end of the suspension period, the external device sends a wake-up instruction 432. This instruction 432 is sent at a time when the IMD 104 should be listening at an instance of the listen operation 436. The IMD 104 sends an acknowledgement 440 after receiving the wake-up instruction 432. If the external device 102 does not receive an acknowledgement 440 immediately after sending the wake-up instruction 432, the external device 102 may repeat the wake-up instruction 432 until the acknowledgement 440 is received.

Upon receiving the acknowledgement 440, the external device 102 then sends the programming instruction 450. The IMD 104 then sends an acknowledgement 452. The external device 102 then proceeds to send an instruction 454 to close the far field session. The IMD 104 then sends an acknowledgement 456. The external device 102 then continues to detect whether a programming request has been received at the query operation 448 and whether the suspension period has ended at the query operation 433.

Where a programming request is not received by the time the end of the suspension period is reached, the external device sends a wake-up instruction 432. This instruction 432 is sent at a time when the IMD 104 should be listening at an instance of the listen operation 436. The IMD 104 sends an acknowledgement 440 after receiving the wake-up instruction 432. Operational flow then proceeds to FIG. 4C and continues as discussed above.

While the external device 102 is detecting whether a programming request has been received at the query operation 448 and whether the suspension period has ended at the query operation 433, the IMD 104 is detecting whether the listen delay period has ended at the query operation 434. When the period of delay has ended, the IMD 104 then activates the far field telemetry communication circuitry 308 to briefly listen for a wake-up signal from the external device 102 at the listen operation 436. The IMD 104 detects whether the wake-up signal has been received at the query operation 438. If a wake-up signal has not been received, the IMD 104 deactivates the far field telemetry communication circuitry 308 and restarts the listen delay period at query operation 434 to delay until the next listen attempt. Where the wake-up signal has been received, the IMD 104 provides the acknowledgement 440 or 441.

While embodiments have been particularly shown and described, it will be understood by those skilled in the art that various other changes in the form and details may be made therein without departing from the spirit and scope of the invention.

What is claimed is:

1. A method of recharging an implantable medical device, comprising:
a first external device communicating with the implantable medical device via a first communication protocol to begin a communication session for a recharge session and providing recharge energy to the implantable medical device according to a data command during the recharge session; and
a second external device communicating with the first external device via a second communication protocol that is different than the first communication protocol and that is a radio frequency protocol to provide the data command.

2. The method of claim 1, wherein the second communication protocol utilizes propagation of a wave including an E-field.

3. The method of claim 2, wherein the second communication protocol comprises a wireless communication protocol for communicating over a distance greater than a distance between the first external device and the implantable medical device.

4. The method of claim 1, wherein the first communication protocol comprises a near field telemetry protocol.

5. A system for recharging an implantable medical device, comprising:
a first external device that communicates with the implantable medical device via a first communication protocol to begin a communication session for a recharge session and providing recharge energy to the implantable medical device according to a data command during the recharge session; and
a second external device that communicates with the first external device via a second communication protocol that is different than the first communication protocol and that is a radio frequency protocol to provide the data command.

6. The system of claim 5, wherein the second communication protocol utilizes propagation of a wave including an E-field.

7. The system of claim 6, wherein the second communication protocol comprises a wireless communication protocol for communicating over a distance greater than a distance between the first external device and the implantable medical device.

8. The system of claim 5, wherein the first communication protocol comprises a near field telemetry protocol.

9. A system, comprising:
an implantable medical device;
a first external device that communicates with the implantable medical device via a first communication protocol to begin a communication session for a recharge session and providing recharge energy to the implantable medical device according to a data command during the recharge session; and
a second external device that communicates with the first external device via a second communication protocol that is different than the first communication protocol and that is a radio frequency protocol to provide the data command.

10. The system of claim 9, wherein the second communication protocol utilizes propagation of a wave including an E-field.

11. The system of claim 10, wherein the second communication protocol comprises a wireless communication protocol for communicating over a distance greater than a distance between the first external device and the implantable medical device.

12. The system of claim 9, wherein the first communication protocol comprises a near field telemetry protocol.

13. The system of claim 9, wherein the first external device comprises a near field inductive driver circuit.

14. The system of claim 9, wherein the first external device comprises an RF antenna.

15. The system of claim 9, wherein the second external device is configured to connect to a telephone network.

16. The system of claim 9, wherein the second external device is a handheld device.

17. The system of claim 9, wherein the second external device is configured to provide programming instructions for the implantable medical device.

18. The system of claim 17, wherein the second external device provides programming instructions for the implantable medical device by the first external device receiving the programming instructions from the second external device and providing the programming instructions to the implantable medical device.

19. The system of claim 9, wherein the second external device communicates with the implantable medical device while the implantable medical device is receiving the recharge energy.

20. The system of claim 19, wherein the second external device communicates with the implantable medical device by the first external device receiving information from the second external device and providing the information to the implantable medical device.

* * * * *